US005338679A

United States Patent [19]

Yuen et al.

[11] Patent Number: 5,338,679
[45] Date of Patent: Aug. 16, 1994

[54] VERTEBRATE POXVORIS EXPRESSION VECTOR UNDER THE CONTROL OF ENTOMOPOXVIRUS SPHEROIDIN GENE PROMOTER

[75] Inventors: Kai-Chung L. Yuen, Ville St. Laurent; Basil Arif, Sualt Ste. Marie, both of Canada

[73] Assignee: Her Majesty the Queen in right of Canada, as represented by National Research Council Canada and Forestry Canada, Quebec, Canada

[21] Appl. No.: 638,742

[22] Filed: Jan. 8, 1991

[51] Int. Cl.$^5$ .................... C12N 7/01; C12N 15/86; C12N 15/11; A61K 39/275
[52] U.S. Cl. ................ 435/235.1; 435/320.1; 424/199.1; 424/232.1; 536/24.1
[58] Field of Search .............. 435/235.1, 320.1, 172.3, 435/69.1; 536/27, 24.1; 424/89, 93; 935/34, 57, 32, 65

[56] References Cited

U.S. PATENT DOCUMENTS 5,077,213  12/1991  Li et al. ..................... 435/235.1

FOREIGN PATENT DOCUMENTS 0330781  9/1989  European Pat. Off. ..... C12N 15/00
0397560  11/1990  European Pat. Off. ..... C12N 15/86
8903429  4/1989  World Int. Prop. O. .... C12P 21/00

OTHER PUBLICATIONS

Esposito, J. J. et al. 1989, *Advances in Veterinary Science and Comparative Medicine*, vol. 33, pp. 195–247, Academic Press, San Diego.
Hall, R. L. et al. 1993 *Virology* vol. 192 pp. 179–187.
Boyle, D. B. 1989, *Research in Virology* vol. 140 No. 5 pp. 483–491.
American Type Culture Collection Catalogue of Animal Viruses 6th Edition. 1990. American Type Culture Collection, Rockville, Md. pp. 135–141.
Hanggi, M. et al. 1986. *EMBO Journal*, vol. 5, pp. 1071–1076.
Banville, M. et al. 1992. *J. Gen. Virol.* vol. 73 pp. 559–566.
Hall, R. L. et al. 1991. *J. Virol.* vol. 65 pp. 6516–6527.
Coupar, B. E. H. et al. 1986. *Eur. J. Immunol.* vol. 16, pp. 1479–1487.
Tsukiyama, K. et al. 1989. *Arch. Virol.* vol. 107 pp. 225–235.
Patel, D. et al. 1986, *Virology* vol. 149 pp. 174–189.
Bilimoria, S. et al. 1979, *Virology* vol. 96 pp. 596–603.
Funahashi, S. et al. 1988. *J. Gen. Virol.* vol. 69 pp. 35–47.
L. Yuen, et al. (Virology, vol. 175, pp 427–433, 1990).
J. A. Cooper, et al. (Virology, vol. 88, pp. 149–165, 1978).
S. Chakrabarti, et al. (Molecular and Cellular Biology, vol. 5, No. 12, pp. 3403–3409, Dec. 1985).

(List continued on next page.)

*Primary Examiner*—Richard A. Schwartz
*Assistant Examiner*—Mary E. Mosher
*Attorney, Agent, or Firm*—Nixon & Vanderhye

[57] ABSTRACT

Disclosed is a recombinant vertebrate F such as vaccinia virus which comprises in its genome (i) spheroidin promoter of entomopoxvirus such as Choristoneura biennis and (ii) at least one structural gene coding for at least one protein foreign to entomopoxvirus and to the vertebrate poxvirus and is capable of expressing the foreign protein gene in a vertebrate tissue culture cell or in a vertebrate animal susceptible to the vaccinia virus. The recombinant virus is capable of expressing the foreign gene at a significantly higher rate due to the presence of the entomopoxvirus spheroidin promoter than the same virus without the entomopoxvirus promoter. The protein may be antigenic or otherwise pharmaceutically useful. Also disclosed vaccine and a process for producing the protein using the recombinant virus.

12 Claims, 5 Drawing Sheets

OTHER PUBLICATIONS

C. F. Wright, et al. (Proc. Natl. Acad. Sci. USA vol. 84, pp. 8883–8887, Dec. 1987).

M. Mackett, et al. (Proc. Natl. Acad, Sci. USA, vol. 79, pp. 7415–7419, Dec. 1982).

P. Chomczynski, et al. (Analytical Biochemistry, vol. 162, pp. 156–159, 1987).

J. P. Weir, et al. (Journal of Virology, vol. 51, No. 3, pp. 662–669, Sep. 1984).

M. A. Cochran, et al. (Journal of Virology, vol. 54, No. 1, pp. 30–37, Apr. 1985).

D. Panicali, et al. (Proc. Natl. Acad. Sci. USA vol. 79 pp. 4927–4931, Aug. 1982).

A. Piccini, et al. (Advances in Virus Research, vol. 34, pp. 43–64, 1989).

B. M. Arif (Advances in Virus Research, vol. 29, pp. 195–211, 1984).

D. D. Patel, et al. (Proc. Natl. Acad. Sci. USA, vol. 85, pp. 9431–9435, Dec. 1988.

C. T. Prideaux, et al. (Virus Research, vol. 16, pp. 43–58, 1990).

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 95 base pairs
        ( B ) TYPE: nucleic acid
        ( C ) STRANDEDNESS: double
        ( D ) TOPOLOGY: linear     ( x i ) SEQUENCE DESCRIPTION: SEQ ID NO:1:

```
GATATTATAA CTTATAATAC CAATATTTTA CTACAACTCT AATAAAAATA GAATAATTTA      60

TTTATTATAA ATAAGCAAAA ATAAAAAAAC AAATA                                 95
```

( 2 ) INFORMATION FOR SEQ ID NO:2:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:2:

```
TAAGTTGGGT AACGCCAGGG TTTTCCC                                          27
```

VERTEBRATE POXVORIS EXPRESSION VECTOR UNDER THE CONTROL OF ENTOMOPOXVIRUS SPHEROIDIN GENE PROMOTER

FIELD OF THE INVENTION

The present invention relates to recombinant chimeric vertebrate poxvirus, such as, vaccinia virus, which contains in its genome a promoter of a different virus and is capable expressing a foreign gene in a vertebrate tissue culture cell or in an animal or human susceptible to the vertebrate poxvirus, to a production process of the recombinant virus and to a use of the recombinant virus.

BACKGROUND OF THE INVENTION

Vaccinia virus is a prototypic member of the group known as poxviruses. Vaccinia virus is widely known and used as an expression vector of foreign gene or portions thereof. The majority of the foreign genes that have been inserted into the vaccinia virus genome encode antigens required for the production of immunity against a variety of infectious agents. It has been used to express a number of genes synthesizing proteins useful in the pharmaceutical/medical sector such as the hepatitis B surface antigen, the influenza virus hemagglutinin and the herpes virus glycoprotein D, neomycin-resistant gene and rabies virus glycoprotein for the purpose of foreign protein and vaccine production. After infection, immune response is elicited against both the vaccinia virus and the foreign protein.

The general procedure to produce recombinant virus expressing the foreign gene is to transfect target cells with a recombinant transfer vector containing the foreign gene of interest and with vaccinia virus. During the replication of the virus in the cell, homologous recombination takes place between some of the viral and the transfected DNAs resulting in a progeny virus containing foreign gene of interest as part of its genome. Classically, foreign DNA was inserted into a region of the vaccinia virus genome such as the endogenous thymidine kinase gene of wild-type virus. Panicali and Paoletti (Proc. Natl. Acad. Sci. U.S.A., 79, 4927–4931 1982) inserted the herpes virus thymidine kinase (TK) gene into a number of vaccinia virus preparations and obtained vaccinia recombinants expressing the herpes virus TK gene. The viral infectivity was shown not to be impaired by the presence of the foreign gene in sharp contrast to SV40 and retrovirus expression systems (Smith and Moss, Gene, 25, 21–28, 1983). These authors also suggested that vaccinia virus expression vector synthesizing proteins of pathogenic organisms might also be employed for medical and vaccination practices. The first candidate vaccine of this type expressed the hepatitis B surface antigen. Since then recombinant vaccinia virus has been employed in the vaccination of rodents against rabies. Piccini and Paoletti (Advances in Virus Research, 34, 43–64, 1989) have recently described the features and advantages of the vaccinia virus expression system and have outlined a number of proteins synthesized by the recombinant virus for the purpose of immunization.

Thus vaccinia virus has been successfully utilized as an expression vector through the insertion of foreign genes into a non-essential region of the viral genome via homologous recombination. However, one serious drawback afflicts the system; vaccinia virus expression vectors are not capable of producing abundant amounts of foreign proteins because of the lack of known strong promoter.

Entomopoxviruses are a group of poxviruses that have been found only in insect species. They posses many of the features of vertebrate poxviruses but are distinguished by the presence of large proteinic cytoplasmic occlusion bodies in which the virions are embedded at the end of the replication cycle (Arif, B.M., Advances in Virus Research, 29, 195–211, 1984). The occlusion bodies are composed mainly of a major vital-coded protein called spheroidin having a molecular weight of approximately 50,000 Daltons (Yuen, Dionne, Arif and Richardson, Virology, for occlusion of the virions and to afford the virions a certain amount of protection against inactivating environmental hazards such as ultraviolet light, desiccation, heat etc. Upon ingestion of the occlusion bodies by a susceptible larva, the gut juices, which are alkaline, dissolve the occlusion bodies thus releasing the virus to cause infection in the larva. Spheroidin is not essential for virus replication but because of its role in viral occlusion and protection, it is abundantly expressed late in the infection cycle. The spheroidin gene of the *Choristoneura biennis* entomopoxvirus has been isolated, cloned and sequenced (Yuen, Dionne, Arif and Richardson, Virology, 175, 427–433, 1990). The gene possesses a powerful promoter required for abundant synthesis of spheroidin. In fact, at the end of the replication cycle of the virus in the insect, approximately 20–50% of the larval protein is spheroidin. This promoter appears to be much more powerful than any of the vaccinia late genes promoters.

Thus the recombinant vertebrate poxvirus expression vectors constructed so far suffer from a drawback that these systems often lack a strong promoter and require very strict conditions in order to obtain adequate expression of the foreign gene. Therefore, engineering of a vertebrate poxvirus expression system powered by a promoter to substantially increase the level of expression has been long desired.

SUMMARY OF THE INVENTION

We investigated the possibility of replacing a vertebrate poxvirus gene promoter with entomopoxvirus spheroidin promoter and surprisingly discovered that the expression of a foreign protein is significantly enhanced when the entomopoxvirus spheroidin promoter is employed as compared with the vertebrate poxvirus gene promoter. This and other discoveries led to the present invention.

Thus, one aspect of the invention provides a recombinant vertebrate poxvirus which comprises in its genome (i) spheroidin promoter of entomopoxvirus and (ii) at least one gene coding for at least one protein foreign to the entomopoxvirus and to the vertebrate poxvirus and is capable of expressing the foreign protein gene in a vertebrate tissue culture cell or in a vertebrate animal susceptible to the vaccinia virus, more efficiently than a recombinant vertebrate poxvirus containing its own gene promoter.

A second aspect of the invention provides a process for producing at least one protein foreign to entomopoxvirus and to vertebrate poxvirus. This process comprises propagating the above-mentioned recombinant vertebrate poxvirus in a vertebrate tissue culture cell infected with the recombinant vertebrate poxvirus by cultivating the infected cell in a cell culture medium until a substantial amount of the protein is produced;

and then collecting the produced protein from the cultured cell.

A third aspect of the invention provides a vaccine that consists essentially of the recombinant vertebrate poxvirus mentioned above in which the foreign protein is at least one immunogenic protein of a pathogen of a vertebrate animal or consists essentially of a cultivation product of a vertebrate tissue culture cell infected with such a recombinant vertebrate poxvirus. The cultivation product contains the immunogenic protein.

DESCRIPTION OF PREFERRED EMBODIMENTS

Examples of the vertebrate poxvirus that may be employed in the present invention include vaccinia, paravaccinia viruses, cowpox viruses, fowlpox viruses and monkeypox viruses. Preferred among those is vaccinia, because of its easy availability and manupilability and so on. Preferred strains of vaccinia include the Western Reserve strain and the Copenhagen strain.

The construct vertebrate poxvirus containing the indicated insect virus promoter is capable of expressing a selected gene or functional portion thereof in vertebrate tissue culture cell or in susceptible vertebrate hosts. These expression vectors consist of vertebrate poxvirus containing a genome that comprises the entomopoxvirus spheroidin promoter. The vertebrate poxvirus/entomopoxvirus spheroidin promoter vector is to be used to express any gene foreign to vertebrate poxvirus and entomopoxvirus. Of particular interest is the synthesis of proteins useful in the medical (i.e pharmaceutical) or veterinary field and also immunogenic proteins that produce immunity (vaccines) to pathogens singly or in multivalent forms. The vector can be used for the synthesis to insect protein or proteins of insect pathogens. The level of synthesis is substantially higher than vaccinia or other vertebrate poxvirus expression vectors that do not contain the spheroidin gene promoter of entomopoxviruses. Insertion of the spheroidin promoter in any vertebrate poxvirus expression vector should give similar results as with vaccinia virus and the spheroidin promoter. We found that the spheroidin promoter functioned in vaccinia virus and was at least approximately 5 times more active than the 7.5 kDa promoter of vaccinia. The promoter was functional in both orientations inserted into tile vaccinia genome. This property is useful when foreign and indicator genes are placed under simultaneous control of one copy of the promoter in vaccinia expression vectors.

The new expression vector is useful in producing foreign proteins such as enzymes, growth factors, immunogenic proteins pathogens of animals and humans that are required for vaccination. Indeed the expression vector can be used potentially to produce proteins of any gene. The vector itself can also be used as vaccine to infect susceptible animals including humans in order to produce immunity against a pathogen from which the foreign gene was obtained. Coding regions of multiple genes can be put under the control of the spheroidin promoter. The vector will then produce fusion products having a plurality of immunogenicities that may serve as multivalent vaccines against a variety of pathogens, or produce a plurality of immunogenic proteins that may also serve as multivalent vaccines.

In the present invention, the spheroidin promoter of any entomopoxviruses can be employed. For its convenience, however, that of *Choristoneura biennis* is particularly preferred. The whole sequence of the spheroidin promoter of *C. biennis* is shown in (SEQ ID No:1). Examples of other entomopoxviruses whose spheroidin promoter may be used according to the present invention include lepidoptera, e.g., *amsacta moorei* EPVs, *Choristoneura fumiferana* EPVs, and *Choristoneura conflictana* EPVs; coleoptera, e.g., *Melolontha melolontha* EPVs; orthoptera, e.g., *Melanoplus sanguinipes* EPVs; and diptera, e.g., *Chironomus luridus* EPVs, and *Aedes aegypti* EPVs.

Examples of such immunogenic proteins that may be produced using the recombinant vertebrate poxvirus vector of the present invention include, among others, hepatitis B virus surface antigen, influenza virus hemagglutin, herpes virus glycoprotein D, rabies virus glycoprotein and HIV antigen. In fact, the production of any immunogenic proteins that can be produced using vertebrate poxvirus such as vaccinia as an expression vector could be enhanced by using the entomopoxvirus promoter according to of the present invention.

The proteins expressed by the recombinant vertebrate poxvirus virus of the present invention may be proteins that are not immunogenic but are useful as medicine in the medical and veterinary field. They include, for example, interferons, interlukins, growth hormones and insulin.

When the protein to be expressed is immunogenic, a suitable vertebrate culture cell may be infected with the recombinant vertebrate poxvirus of the present invention and the infected cell is cultured in a suitable culture medium so as to propagate the virus until a substantial amount of the protein is produced. Optionally after removing certain undesirable matters, the protein may be used as vaccine. Alternatively, the recombinant vertebrate poxvirus such as vaccinia virus itself may be used as vaccine in certain circumstances.

When the protein to be expressed is other than an immunogenic protein, usually the vertebrate culture cell infected with the virus is cultured until a substantial amount of the protein is produced and then the protein is purified.

Methods of the infection, vertebrate culture cells useful for the production of the desired protein and method of purification are generally well known in the art. Examples of preferred vertebrate culture cells useful for this purpose include TK minus and CV-1 cells.

In order to construct the recombinant vertebrate poxvirus according to the present invention, at first the entomopoxvirus spheroidin promoter gene is provided. The gene of *C. biennis* spheroidin promoter gene is already known and this gene may be chemically synthesized or may be cut out of the *C. biennis* entomopoxvirus spheroidin gene (which is reported by the inventors in Virology 175, 427–433 (1990), the entire content thereof being incorporated herewith by reference) using an appropriate endonuclease. The entire sequence (SEQ ID NO: 1) is shown on the page immediately prior to the claims. It is not necessary, however, to include the entire sequence (i.e. from the 1 position to the 95 position) but only the essential portion (which appears to be from the 35 position to the 75 position) is necessary to sufficiently enhance the expression of the foreign protein. In addition, modified sequences equivalent to the essential portion or to the whole native sequence would also work essentially in the same way.

Then the thus-obtained promoter is combined with a gene coding for at least one protein that is foreign to entomopoxvirus and to vertebrate poxvirus, usually with the promoter upstream of the gene coding for the foreign protein. It is preferable that the gene coding for the foreign protein includes a marker gene region to facilitate the identification and isolation (or screening or cloning) of the recombinant vertebrate poxvirus.

The combined promoter/foreign gene are then inserted into the genome of vertebrate poxvirus. The method for insertion of such a foreign gene is well known in the art, for example, in "General Protocol for the Insertion of Foreign Genes into the Vaccinia Virus Genome" at pages 50 to 54 of Advances In Virus Research, 34 (1989) which is incorporated herewith by reference. Namely, specific vertebrate poxvirus gene sequences are cloned such that they flank the foreign gene and direct the foreign gene to the homologous sequences on the vertebrate poxvirus genome. An appropriate cell line is infected with the foreign gene flanked by the specific vertebrate poxvirus gene sequences and simultaneously with vertebrate poxvirus virus that does not have the foreign gene. In the infected cell, during DNA replication, the vertebrate poxvirus virus genome incorporates the foreign gene into its own. Among propagated virus, a virus in which the genome has incorporated the foreign gene is detected, screened and selected by a known method, for example, using the marker, a DNA hybridization technique, an enzyme assay or a drug resistance.

Thus constructed recombinant vertebrate poxvirus may be propagated in a suitable vertebrate tissue culture cell by cultivating the cell infected with the virus in a suitable culture medium. The suitable vertebrate tissue culture cells, the suitable culture medium and culture conditions are generally well-known in the art. No special cells, medium or conditions are necessary for propagating the recombinant vertebrate poxvirus the present invention. Preferred cells include TK minus cells and CV-1 cells.

Where required, the propagated vertebrate poxvirus may be isolated and purified from the culture medium. One of such methods is described by Cooper and Moss (Virology, 88, 149–165, 1978).

Further where required, the proteins produced by the recombinant vertebrate poxvirus may be purified by any suitable methods that are well known in the art.

BRIEF DESCRIPTION OF THE DRAWINGS

FIG. 1 shows a gene map of plasmid pGal constructed in Example ;

FIG. 2 is a graph showing time course expression β-galactosidase in CV-1 cells infected with vSph 95 and v7.5 kDa recombinant viruses;

FIG. 3 shows mapping of 5' terminus of the β-galactosidase transcript in sVph 95-infected cells;

FIG. 4 shows dot blot analysis of β-galactosidase transcripts in CV-1 cells infected with vSph 95 or v7,5 kDa;

FIG. 5 is a graph showing time course expression of β-galactosidase in CV-1 cells infected with several recombinant viruses; and FIG. 6 shows SDS-polyacrylamide gel analysis of β-galactosidase protein synthesized in recombinant viruses.

DETAILED DESCRIPTION OF THE DRAWINGS

FIG. 1 shows construction of spheroidin-vaccinia recombinant viruses- Plasmid pGal was constructed as described in Example 1. The plasmid contains a unique EcoRI site for the insertion of promoter sequences, The β-galactosidase gene is flanked by the vaccinia thymidine kinase gene and its neighboring sequences.

FIG. 2 shows time course expression of β-galactosidase in CV-1 cells infected with vSph95 and v7.5 kDa recombinant viruses, CV-1 cells grown in 24-well plates were infected with either vSph 95 or v7.5 kDa at 10 m.o.i. Infected cells were harvested at various times post-infection and β-galactosidase activities were measured as described in Example 1.

FIG. 3 shows mapping of 5' terminus of the β-galactosidase transcript in vSph 95-infected cells, Total RNA was isolated from CV-1 cells infected with 5 m.o.i. of vSph 95 at 16 h.p.i. β-galactosidase transcript was mapped either by S1 or by primer extension.

(A) S1 mapping was performed as described in Example 1 using a 5' labeled 330 nt Ciai-PvuII DNA fragment. S1 resistant DNA fragment were analyzed in a 6% sequencing gel.

Lane a: MspI digested pBR322 DNA molecular markers expressed in number of nucleotides (nt);

Lane b: transfer RNA control;

Lane c: 30 μg of total RNA from vSph 95-infected cells.

(B) Primer extension of the β-galactosidase transcript was performed as described in Example 1 using an oligonucleotide about 160 nt from the EcoRI site of pGal. Primer extended products were analyzed in a sequencing gel.

Lane a: 25 μg or lane b: 50 μg of total RNA from vSph 95-infected cells;

Lane c: Mspl-digested pBR322 DNA markers.

DNA sequence around the 5' terminus is shown, with the 5' terminal nucleotides determined by S1 and primer extension (PE) underline, FIG. 4 shows a dot blot analysis of β-galactosidase transcripts in CV-1 cells infected with vSph 95 or v7.5 kDa. Total RNAs from CV-1 cells infected with either vSph 95 or v7.5 kDA viruses were purified at 16 h.p.i. as described in Example 1. 20 μg of total RNAs were applied to each well (done in duplicates) and hybridization was carried out at 65 C using a $^{32}P$-labeled 3.2 kb XbaI-DraI fragment containing the entire β-galactosidase gene. Total RNAs were obtained from cells infected with: (a) wild-type vaccinia virus; (b) and (c) vSph 95 recombinant; (d) and (e) v7.5 kDa recombinant virus.

FIG. 5 shows time course expression of β-galactosidase in CV-1 cells infected with several recombinant viruses. CV-1 cells grown in 24-well plates were infected with either v7.5 kDa, vSph 95, vSph 33 or vSph 15 viruses at a m.o.i. of 10, β-galactosidase activities were measured at various times post-infection.

FIG. 6 shows SDS-polyacrylamide gel analysis of β-galactosidase protein synthesized in recombinant viruses. Cell lysates (approximately $4\times10^4$ cells) from recombinant virus-infected CV-1 cells were electrophoresed in a 10% SDS-polyacrylamide gel and proteins were detected by Coomassie blue staining. Lane a: protein molecular markers in kDa; lane b: uninfected cells; lance c: wt vaccinia virus infected-cells, 12 h.p.i., lane d: 16 h.p.i., lane e: 20 h.p.i.; lane f: vSph 95-infected cells, 12 h.p.i., lane g: 16 h.p.i., lane h: 20 h.p.i.; lane i: vSph 33-infected cells, 12 h.p.i., lane j: 16 h.p.i., lane k: 20 h.p.i.; lane 1: vSph 15-infected cells, 12 h.p.i., lane m: 16 h.p.i., lane n: 20 h.p.i.: lane o: v7.5 kDa-infected cells, 12 h.p.i., lane p: 16 h.p.i., and lane q: 20 h.p.i.

Arrow indicates position of the β-galactosidase protein.

In the following, an example is presented, however, it should be understood that the present invention is not limited to the example.

EXAMPLE 1

Figure 1:
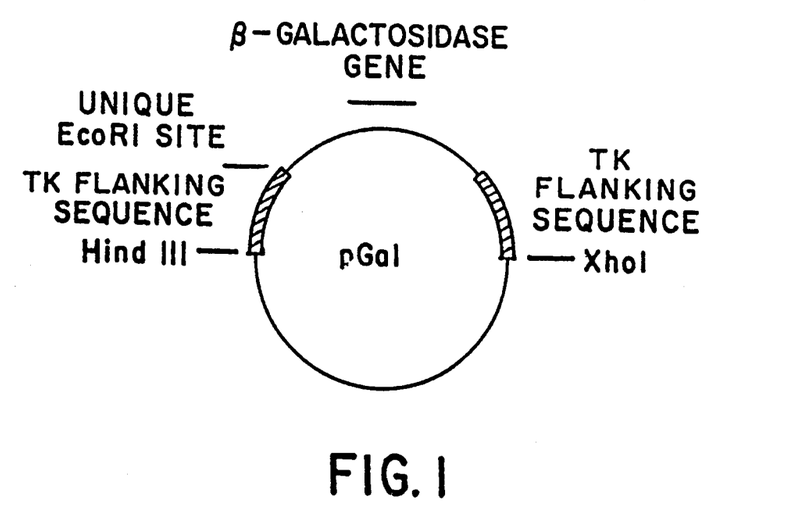

Construction of spheroidin-vaccinia expression vectors and recombinant viruses Ninety five (95) nucleotides of DNA sequence at the 5' non-coding region of the *C. biennis* entomopoxvirus spheroidin gene (SEQ ID NO: 1) was chemically synthesized and inserted into a vaccinia expression vector interrupting the vaccinia thymidine kinase gene. The bacterial beta galactosidase gene, a reporter gene, was engineered downstream of this sequence. Its presence turns recombinant viral plaques blue colour thus facilitating the identification of recombinant vaccinia viruses. A plasmid was constructed by inserting a Klenow-blunted 3.2kb XbaI-DraI DNA fragment containing the entire beta galactosidase gene open reading frame at the EcoRI site (also blunted) of a pBR328-based plasmid containing the HindIII-XhoI fragment of the HindIII J fragment of vaccinia (see FIG. 1). The resulting plasmid, called pGal, retains the unique EcoRI site for insertion of other DNA fragments. The beta galactosidase gene in the pGal interrupts the thymidine kinase gene of vaccinia virus thus enabling further selection of recombinant virus by blue plaques. To insert the spheroidin 5' non-coding region ( which contains the promoter ) into pGal, complementary oligonucleotides with terminal EcoRI restriction site (see SEQ ID NO:1) were chemically synthesized and cloned at the EcoRI site of pGal. Recombinant vaccinia viruses containing the spheroidin promoter and the beta galactosidase gene were identified and purified according to the procedure described by Chakrabarti and coworkers (Molecular and Cell Biology, 5, 3403-3409, 1985). The vaccinia virus used in these studies was the Western Reserve Strain. The cell types in which the virus was propagated were the TK minus or CV-1 cells. Virus propagation and purification was carried out as described by Cooper and Moss (Virology, 88, 149-165, 1978). The recombinant vaccinia virus was submitted for deposit at ATCC Rockville, Md. (depositor's strain designation: SLZ103) on Dec. 11, 1990, received by ATCC on Dec. 12, 1990 and deposited under Accession Number VR2292.

β-Galactosidase enzyme assay. TK cells or CV-1 cells grown in 24-well plates (Corning) were infected with recombinant vaccinia viruses at a multiplicity of infection (m.o.i.) of 10. At appropriate times post-infection, cells were scraped and transferred in the infection medium into Eppendorf tubes. Cells were pelleted by centrifugation, washed once with phosphate buffer saline (PBS: 100mn $KH_2PO_4$, pH 7.2, and 150 mn NaCl) and resuspended in 50 μl of FT buffer (250 mM sucrose, 10 mM Tris-HCl, pH 7.4, 10 mM EDTA). After freeze-thawing three times, cell debris were removed by centrifugation at 10,000 rpm for 10 min. The supernatant was used in β-galactosidase enzyme assay. Routinely, 20 1 of the supernatant was added to 180 μl of Z buffer (60 mM $Na_2PO_4$, 40 mM $NaH_2PO_4$, 10 mM KCl, 1 mM $MgSO_4$, 50 mM ⊖-mercaptethanol, adjust to pH 7.0) in a fresh eppendorf tube. To start the enzyme reaction, 40 μl of the enzyme substrate pNPG (4mg/ml, Bethesda Research Laboratory) was added to the reaction mix and incubation was carried out at 30° C. for 2 to 3 min. When a yellow coloration developed, 100 μl of 1 M sodium carbonate was added to measuring the optical density at 420 nm.

Isolation of total RNA. CV-1 or TK cells were infected with recombinant viruses at 5 m.o.i. Total RNA was purified from virus-infected cells according to a previously described method (Chomczynski and Sacchi, 1987 "Single-step method of RNA isolation by acid quanidinium thiocyanate-phenol-chloroform extraction", Anal. Biochem. 162, 155-159.

5' Mapping of β-galactodidase transcripts. S1 mapping of 5' termini of β-galactosidase transcripts were performed essentially as previously described (Weir and Moss, 1984 "Regulation of expression and nucleotide sequence of a late vaccinia virus" J. Virol. 51, 662,669). A 330 nucleotide (nt) ClaI-PvuII DNA fragment spanning the entire spheroidin promoter and including upstream vaccinia viral and downstream β-galactosidase sequences was end-labeled at the PvuII site with [$\gamma-^{32}P$] ATP (Amersham, 3000Ci/mMole) and T4 DNA polynucleotide kinase (Pharmacia). About 20,000 cpm of this radioactive probe was incubated with 30 μg of appropriate total RNA at 42° C. for 2h and then S1 nuclease (Pharmacia) was added at a concentration of 500 μ/ml. Protected DNA fragments were ethanol precipitated and analyzed on a 6% sequencing gel.

Primer extension was performed using an oligonucleotide (TAAGTTGGGTAACG-CCAGGGTTTTCCC) (SEQ ID NO: 2) 160 nt from the EcoRI site of plasmid pGal. [$\gamma-^{32}P$]ATP labeled oligonucleotide was annealed with 50 g of total RNA in a 10 μl volume containing 10 mM Tris-CH1, pH 7.4, and 250 mM KCl. The reaction mix was heated at 65° C. for 10 min and then cooled slowly at room temperature for 30 min. After annealing, 3 μl of the reaction mix was added to 3.3 μl of reverse transcription buffer (25 mM TriS-HCl, pH 8.0, 16 mM $MgCl_2$, 8 mM DTT, 0.4 mM each of the four deoxyribonucleotides) containing 8 units of reverse transcriptase (Pharmacia). The reverse transcription reaction was performed at 42° C. for 45 min., and then stopped by the addition of equal volume of sequencing formamide stop buffer. The primer extension products were analyzed on a 6% sequencing gel.

Dot blot analysis of β-galactosidase transcripts. Dot blot analysis of β-galactosidase transcripts was performed by applying 20 μof total RNA from recombinant virus-infected cells onto nitrocellulose membrane (Schleicher & Schuell) using a multi-well filtration manifold (Schleicher & Schuell). β-Galactosidase transcripts were detected using a 3.2 kb $^{32}P$-labelled Xba I-Dra I DNA fragment containing the entire β-galactosidase gene. Hybridization was carried out at 65° C. overnight in 0.1% sodium dodecyl sulfate (SDS) and 6X SSC (90 mM sodium citrate, ana 900 mM sodium chloride). The membranes were washed in 2X SSC before exposing to Kodak ® XAR5 x-ray film.

Gel electrophoresis. SDS-polyacrylamide gels for protein analysis were performed as described by Laemmli (Laemmli, 1970, "Cleavage of structural protein during the assembly of the head of bacteriophage T4", Nature (London) 27, 680-685) .

Figure 2:
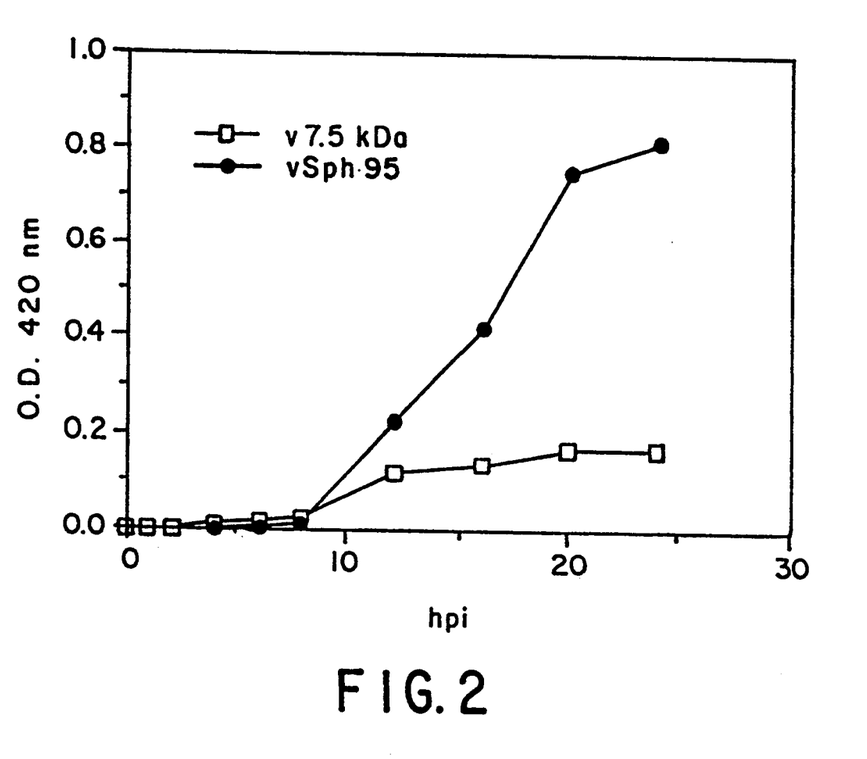

Results

β-Galactosidase expression in a recombinant vaccinia virus under the transcriptional control of the CbEPV spheroidin 5' non-coding sequence A recombinant vaccinia virus containing 95 nt of the 5' non-coding sequence of the CbEPV spheroidin gene inserted upstream of the bacterial β-galactosidase gene in the plasmid pGal (see FIG. 1) was constructed and purified. This recombinant virus, designated vSph 95, was identified by its ability to form blue plaques in the presence of the substrate x-gal. To detect and analyze the production of β-galactosidase, CV-1 cells were infected with vSph 95 at a m.o.i. of 10, and cells were harvested at various times post-infection. β-galactosidase activities were quantitated and the results are shown in FIG. 2. As a control a 300 nt EcoRI DNA fragment containing the entire vaccinia 7.5 kDa promoter (Cochran et.al., 1984, "In vitro mutagenesis of the promoter region for a vaccinia virus gene: Evidence of tandem early and late regulatory signals, J. Virol. 54, 30–37") was inserted at the EcoRI site in pGal, thus placing the β-galactosidase gene under the control of the 7.5 kDa promoter. The resulting virus was designated v7.5 kDa, As previously reported, p7.5 kDA is active both early and late in vaccinia virus infection (Cochran et.al., 1984, ibid). β-galactosidase activity was detected as early as 4 h.p.i. with v7.5 kDa and the enzyme level continued to increase up to 24 h .p. i. , the last time point of the experiment (FIG. 2 ). This activity profile agreed well with the predicted early-late nature of the 7.5 kDa promoter. On the contrary, no significant β-galactosidase activity was detected in vSph 95-infected cells until 8 h.p.i. However, the enzyme level in vSph 95-infected cells increased at a much higher rate than with v7.5 kDa. At 24 h.p.i., β-galactosidase level in the vSph 95-infected cells was about 4 to 5 folds higher than that of v7.5 kDa (FIG. 2).

Figure 3:
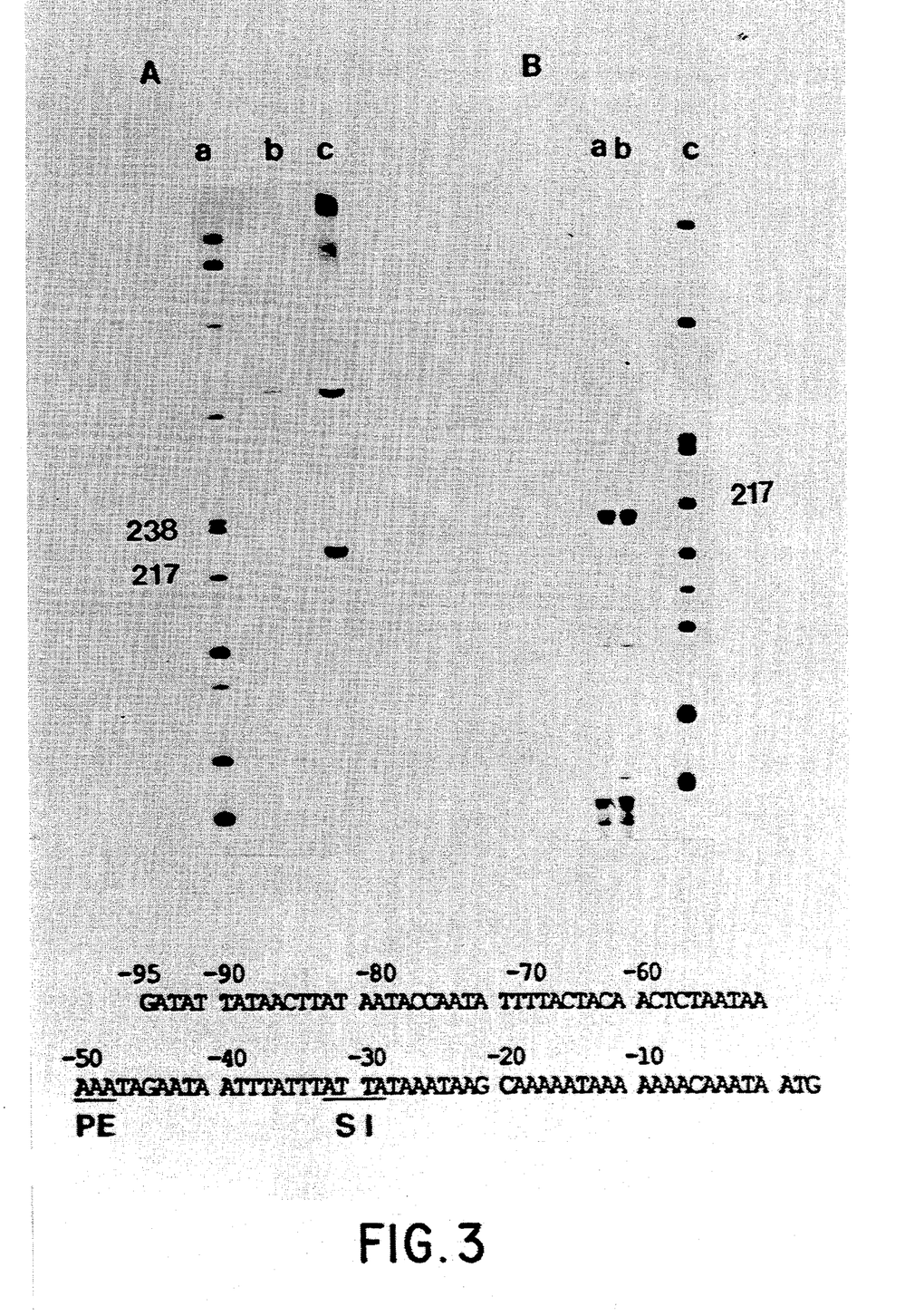

To confirm that the β-galactosidase gene was under the transcriptional control of the spheroidin sequence, we proceeded to map the 5' terminus of the β-galactosidase transcript by SI analysis. A 330 nt ClaI-PvuII DNA fragment containing the entire spheroidin sequence and part of the 5' end sequence of the β-galactosidase gene was end-labeled with [γ-$^{32}$P]ATP and T4 polynucleotide kinase at the PvuII site and then used in 5' S1 mapping of the β-galactosidase transcript. When S1 nuclease resistant DNA were electrophoresed in a sequencing gel, two major DNA fragments about 230 nt in length were detected (FIG. 3A). As with most late vaccinia transcripts analyzed to date, the 5' terminus of the β-galactosidase transcript resides near the consensus TAAAT motif (See SEQ ID NO: 1).

The 5' end of the β-galactosidase transcript was also analyzed by primer extension using an oligonucleotide about 160 nt from the EcoRI site of pGal. Sequencing gel data of the primer extension products located the 5' end of the transcript about 15 to 20 nt upstream of that obtained by S1 mapping (FIG. 3b). This discrepancy can be explained by the presence of oligo(A) sequence at the 5' end of vaccinia late transcripts as previously reported (Wright and Moss, 1987, "In vitro synthesis of vaccinia virus late mRNA containing a 5' poly(A) leader sequence," Proc. Natl. Sci. USA 84, 8883–8887; Bertholet et .al. , 1987 "Vaccinia virus produces late mRNAs by discontinuous synthesis", Cell 50, 153–162; Schwer et.al., 1987 "Discontinuous transcription of RNA processing of vaccinia virus late messengers results in a 5' poly(A) leader", Cell 50, 163–169).

Dot blot analysis of the β-galactosidase transcripts

To determine whether the difference in β-galactosidase productions between the vSph 95 and v7.5 kDa viruses was due to the difference in their transcript levels, CV-1 cells were infected with the two recombinants at 10 m.o.i. and total RNAs were purified from infected cells at 16 h.p.i Amounts of β-galactosidase transcripts were quantitated by dot blot hybridization using a $^{32}$P-labeled DNA fragment containing the entire β-galactosidase gene. Dot blot results clearly indicated the greater abundancy of transcript in vSph 95-infected cells (FIG. 4, demonstrating that the spheroidin sequence functioned as a stronger promoter than the vaccinia 7.5 kDa promoter.

Further analysis of the spheroidin promoter

Figure 5:
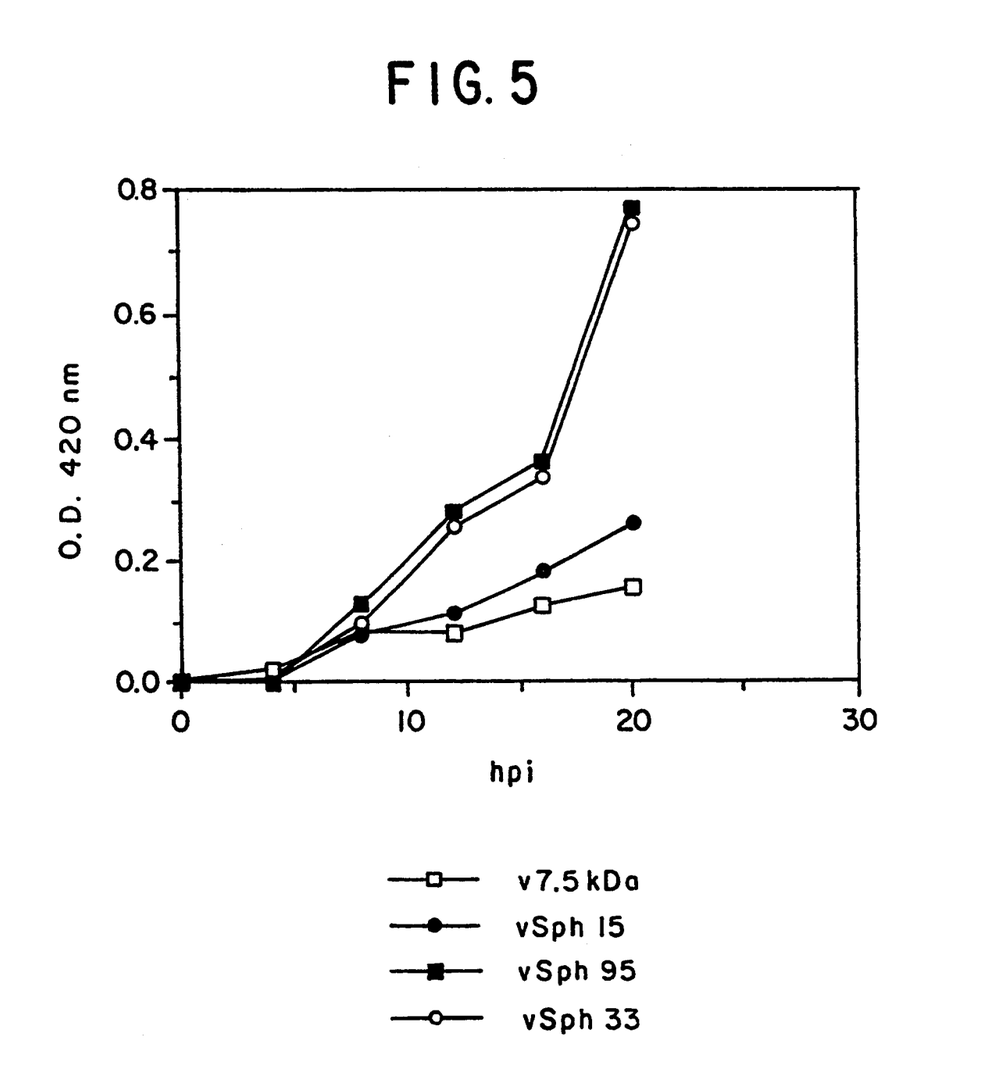
Figure 6:
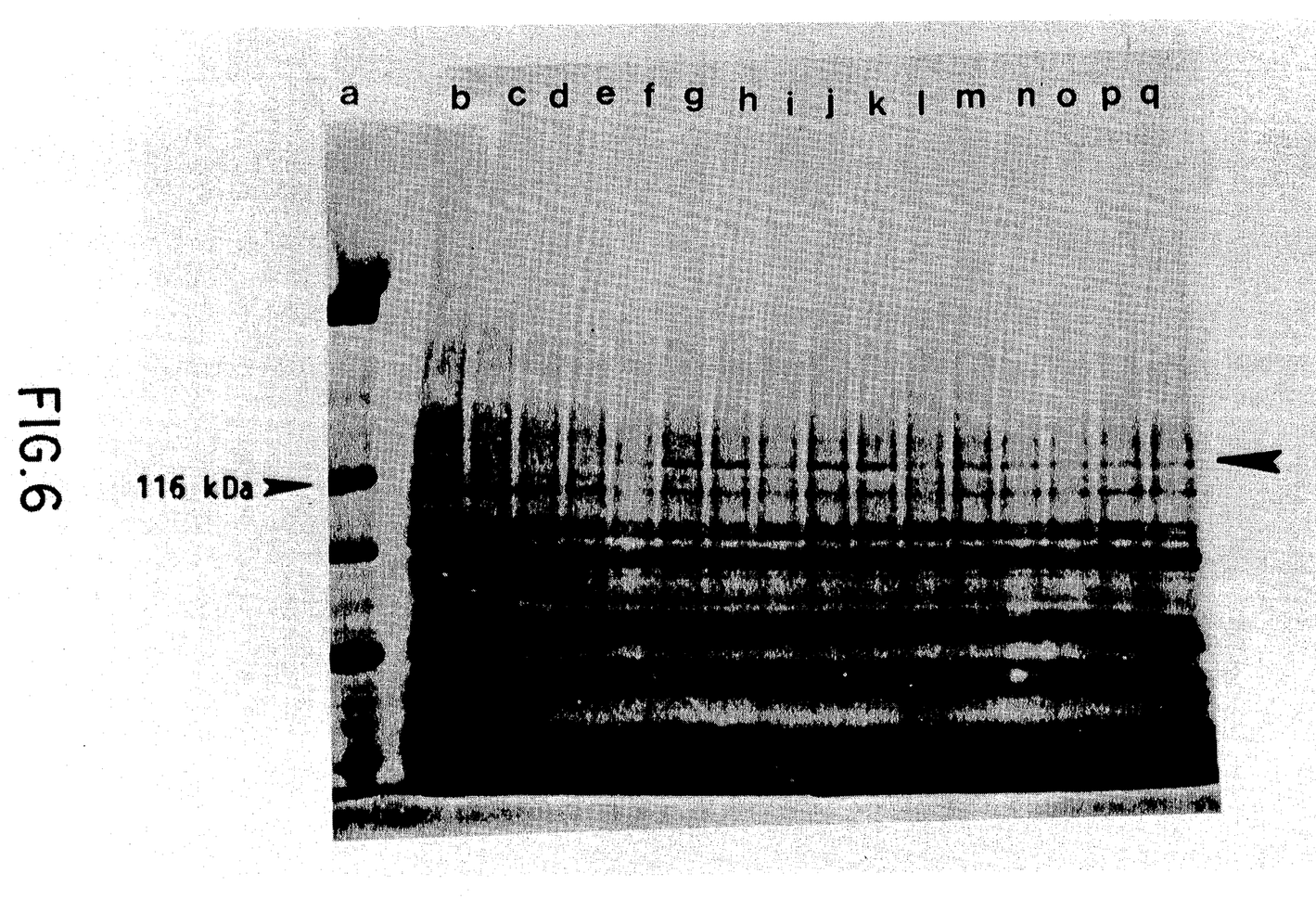

Previous reports suggested that DNA sequences about 30 nt upstream of and including the TAAAT motif constituted full activity strength in vaccinia late promoters (Hanggi et.al. , 1986, "Conserved TAAAT motif in vaccinia virus late promoters: overlapping TATA box ana site of transcription initiation", The EMBO Journal 5, 1071–1076). To investigate whether this phenomenon also applies to the spheroidin promoter, two new spheroidin-vaccinia recombinant viruses were constructed. One virus, designated vSph 15, contains DNA sequence spanning the 95 to 53 position of the spheroidin 5' non-codin region (see SEQ ID NO: 1); the other virus, designated vSph 33, contains sequence from the 75 to 35 positions. VSph 15 contains the TAAAT motif and 15 upstream nucleotides as well as some downstream sequences; while vSph 33 contains the TAAAT motif and 33 upstream nucleotides. When these two new recombinant viruses were used to infect CV-1 cells and the amounts of β-galactosidase in infected cells were assayed, it was shown that while vSph 33 synthesized the enzyme at level similar to that of vSph 95, vSph 15 only produced about 25% of β-galactosidase compared to the other two viruses (See FIG. 5).

These results demonstrated that the vSph 33 promoter contains all the essential information encoded in the 95 nt spheroidin 5' non-coding sequence, while vSph 15 only constitutes a partially functional promoter. The data also suggested that sequences downstream of the TAAAT motif in the spheroidin 5' non-coding region plays no significant role in determining promoter strength.

SDS-polyacrylamide gel electrophoresis of recombinant virus-infected cells

Figure 4:
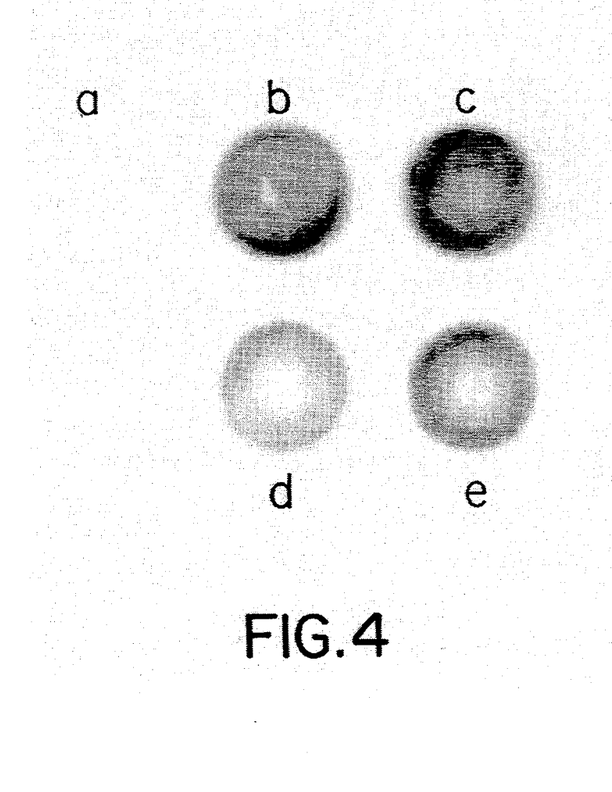

To demonstrate the synthesis of authentic β-galactosidase protein with predicted size in these recombinant virus-infected cells, portions of the infected-cell lysates used in β-galactosidase enzyme assays were analyzed by SDS-polyacryl-amide gel electrophoresis. Coomassie blue staining of the proteins clearly showed the presence of a 120 kDA protein in cells infected with the recombinant viruses but not in uninfected or wild-type (wt) vaccinia virus-infected cells. This 120 kDA protein comigrated with the β-galactosidase protein (labeled as 116 kDa fragment) in the molecular marker mix, and was synthesized late in infected cells. Furthermore, the relative amounts of this protein synthesized in these difference recombinant virus-infected cells agreed with the β-galactosidase activity levels previously determined (FIG. 4). All these data combined suggested that the 120 kDa protein is the authentic β-galactosidase enzyme.

Discussion

We demonstrated the ability of a DNA fragment in the 5' non-coding region of the CbEPV spheroidin gene to function as an efficient promoter in the mammalian vaccinia expression system. One interesting feature of the spheroidin promoter is its ability for function bidirectionally. When the spheroidin promoter was inserted in the reverse orientation upstream of the β-galactosidase gene in pGal, we detected production of observable, but low level of the enzyme. It turns out that when inserted in the opposite orientation, the spheroidin sequence also contains a TAAAT motif, the minimum requirement for any late vaccinia promoter. The bidirectionality of the spheroidin promoter may facilitate construction of poxvirus expression vectors were foreign and indicator genes can be placed under simultaneous control of one copy of the promoter.

The spheroidin promoter activity in vaccinia does not appear to be as strong as we would expect it to be in its natural insect host in which the protein constitutes the majority of all late viral proteins. We suspect that either the insect hosts or other viral factors may play some roles in determining the activity of the spheroidin promoter. Another possible explanation is the difference in the environments between mammalian cells and insect cells in which the CbEPV spheroidin promoter normally functions. When we introduced the CbEPV spheroidin promoter and its coding sequence into vaccinia, we failed to detect appreciable quantity of spheroidin protein in the recombinant virus-infected cells. This is likely not due to the lack of mRNA transcription. Instead we suspect that this phenomenon might be due to a post-transcriptional event such as the instability of the spheroidin protein in mammalian cells.

---

---

What we claim as our invention is:

1. A recombinant vertebrate poxvirus which comprises in its genome (i) a bidirectional spheroidin promoter of entomopox *Choristoneura biennis* and (ii) at least one heterologous gene coding for at least one protein, said heterologous gene or genes being operatively linked to said bidirectional *Choristoneura biennis* promoter.

2. The recombinant vertebrate poxvirus, according to claim 1, wherein the vertebrate poxvirus is vaccinia virus.

3. The recombinant vaccinia virus according to claim 2, wherein the said gene or genes code for at lest one immunogenic protein of a pathogen of an animal.

4. The recombinant vaccinia virus according to claim 3, wherein the said genes code for a plurality of the immunogenic proteins, or said gene codes for a fused protein having a plurality of immunogenicities.

5. The recombinant vaccinia virus according to claim 2, wherein the entomopox spheroidin promoter comprises a DNA sequence of bases 35 to 75 of (SEQ ID NO: 1).

6. A recombinant vaccinia virus according to claim 2, which comprises in a non-essential region of its genome:
    (i) spheroidin promoter of *Choristoneura biennis* entomopoxvirus which comprises a DNA sequence of bases 35 to 75 of (SEQ ID NO: 1) of the 5' non-coding region of the *Choristoneura biennis* entomopoxvirus spheroidin gene, and
    (ii) operatively linked to the entomopoxvirus spheroidin promoter downstream of the entomopoxvirus spheroidin promoter, at least one heterologous and to vaccinia virus.

7. The recombinant vaccinia virus according to claim 6, wherein the entomopoxvirus spheroidin promoter and the foreign protein gene are placed interrupting the vaccinia thymidine kinase gene.

8. The recombinant vaccinia virus according to claim 6, wherein the entomopoxvirus spheroidin promoter comprises a DNA sequence of bases 1 to 95 of (SEQ ID NO: 1).

9. The recombinant vaccinia virus according to claim 6, which is based on Western Reserve strain.

10. A vaccine consisting essentially of: a recombinant vertebrate poxvirus which comprises in its genome (i) a bidirectional spheroidin promoter of entomopoxvirus *Choristoneura biennis* and (ii) at least one heterologous gene coding for at least one immunogenic protein of a pathogen of a vertebrate animal, said heterologous gene being operatively linked to said bidirectional *Choristoneura biennis* spheroidin promoter, or a cultivation product of a vertebrate poxvirus, the cultivation product containing said immunogenic protein and said recombinant vertebrate poxvirus.

11. The vaccine according to claim 10, wherein the vertebrate poxvirus is vaccinia virus.

12. The vaccine according to claim 11, wherein the said promoter comprises a DNA sequence of bases 35 to 75 of (SEQ ID NO: 1) and is positioned upstream of the gene coding for the heterologous immunogenic protein.

* * * * *

UNITED STATES PATENT AND TRADEMARK OFFICE
CERTIFICATE OF CORRECTION

PATENT NO. : 5,338,679
DATED : August 16, 1994
INVENTOR(S) : Kai-Chung L. Yuen, et al It is certified that error appears in the above-indentified patent and that said Letters Patent is hereby corrected as shown below:

On the title page, and column 1, line 1-4, the title should read —VERTEBRATE POXVIRUS EXPRESSION VECTOR UNDER THE CONTROL OF ENTOMOPOXVIRUS SPEROIDIN GENE PROMOTER—.

Column 12, claim 6, line 10, after "heterologous" insert —gene coding for at least one protein foreign to entomopoxvirus—.

Column 14, claim 10, line 9, after "vertebrate" insert —tissue culture cell infected with the said recombinant vertebrate—.

Signed and Sealed this

Twenty-seventh Day of December, 1994

Attest:

BRUCE LEHMAN

*Attesting Officer*  *Commissioner of Patents and Trademarks*

UNITED STATES PATENT AND TRADEMARK OFFICE
CERTIFICATE OF CORRECTION

PATENT NO. : 5,338,679
DATED : August 16, 1994
INVENTOR(S) : Kai-Chung L. Yuen, et al It is certified that error appears in the above-indentified patent and that said Letters Patent is hereby corrected as shown below:

On the title page, and column 1, line 1-4, the title should read
—VERTEBRATE POXVIRUS EXPRESSION VECTOR UNDER THE CONTROL OF ENTOMOPOXVIRUS SPHEROIDIN GENE PROMOTER —.

Column 12, claim 6, line 10, after "heterologous" insert —gene coding for at least one protein foreign to entomopoxvirus—.

Column 14, claim 10, line 9, after "vertebrate" insert —tissue culture cell infected with the said recombinant vertebrate—.

This certificate supersedes Certificate of Correction issued December 27, 1994.

Signed and Sealed this

Twenty-eight Day of February, 1995

Attest:

BRUCE LEHMAN

Attesting Officer        Commissioner of Patents and Trademarks